(12) United States Patent
Lockwood et al.

(10) Patent No.: US 11,197,868 B2
(45) Date of Patent: Dec. 14, 2021

(54) PREVENTION OF PRETERM BIRTH (PTB) BY INHIBITION OF FKBP51

(71) Applicant: UNIVERSITY OF SOUTH FLORIDA, Tampa, FL (US)

(72) Inventors: Charles Lockwood, Tampa, FL (US); Özlem Guzeloglu-Kayisli, Wesley Chapel, FL (US); Ümit Kayisli, Wesley Chapel, FL (US); Frederick Schatz, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/488,494

(22) PCT Filed: Feb. 23, 2018

(86) PCT No.: PCT/US2018/019505
§ 371 (c)(1),
(2) Date: Aug. 23, 2019

(87) PCT Pub. No.: WO2018/156945
PCT Pub. Date: Aug. 30, 2018

(65) Prior Publication Data
US 2019/0388433 A1    Dec. 26, 2019

Related U.S. Application Data

(60) Provisional application No. 62/463,430, filed on Feb. 24, 2017.

(51) Int. Cl.
*A61K 31/5575* (2006.01)
*A61P 15/06* (2006.01)

(52) U.S. Cl.
CPC .......... *A61K 31/5575* (2013.01); *A61P 15/06* (2018.01)

(58) Field of Classification Search
CPC ..................... A61K 31/5575; A61P 15/06
See application file for complete search history.

(56) References Cited

U.S. PATENT DOCUMENTS

2012/0046261 A1    2/2012   Manuck et al.

FOREIGN PATENT DOCUMENTS

WO            2012052953 A1    4/2012

OTHER PUBLICATIONS

Shibata et al. The Journal of Biological Chemistry, 2002, vol. 277, No. 12, pp. 10459-10466.*
Berry et al. (Molecular Pharmacology, 2005, vol. 68, No. 1, pp. 169-178.*
Sykes et al.; "Anti-inflammatory prostaglandins for the prevention of preterm labour"; Reproduction Review 2014; 12 pages.
Pirianov et al.; "The Cyclopentenone 15-Deoxy-Δ 12,14-Prostaglandin J2 Delays Lipopolysaccharide-Induced Preterm Delivery and Reduces Mortality in the Newborn Mouse"; Endocrinology, Feb. 2009p 8 pages.
Agrawal, Neema, et al. "RNA interference: biology, mechanism, and applications" Microbiol. Mol. Biol. Rev. 67.4 (2003): 657-685.
Ambros, Victor. "The functions of animal microRNAs." Nature 431.7006 (2004) 350-355.
Bartel, David P. "MicroRNAs: genomics, biogenesis, mechanism, and function." cell 116.2 (2004): 281-297.
Binder, Elisabeth B., et al. "Association of FKBP5 polymorphisms and childhood abuse with risk of posttraumatic stress disorder symptoms in adults." Jama 299.11 (2008): 1291-1305.
Binder, Elisabeth B., et al. "Polymorphisms in FKBP5 are associated with increased recurrence of depressive episodes and rapid response to antidepressant treatment." Nature genetics 36.12 (2004): 1319.
Blair, Laura J., et al. "Accelerated neurodegeneration through chaperone-mediated oligomerization of tau." The Journal of clinical investigation 123.10 (2013): 4158-4169.
Blencowe, Hannah, et al. "National, regional, and worldwide estimates of preterm birth rates in the year 2010 with time trends since 1990 for selected countries: a systematic analysis and implications." The lancet 379.9832 (2012): 2162-2172.
Boonyaratanakornkit, Viroj, et al. "Progesterone receptor contains a proline-rich motif that directly interacts with SH3 domains and activates c-Src family tyrosine kinases." Molecular cell 8.2 (2001): 269-280.
Boonyaratanakornkit, Viroj, et al. "The role and mechanism of progesterone receptor activation of extra-nuclear signaling pathways in regulating gene transcription and cell cycle progression." Steroids 73.9-10 (2008): 922-928.
Condon, Jennifer C., et al. "Up-regulation of the progesterone receptor (PR)-C isoform in laboring myometrium by activation of nuclear factor-κB may contribute to the onset of labor through inhibition of PR function." Molecular endocrinology 20.4 (2006): 764-775.
Daniel, Andrea R., Christy R. Hagan, and Carol A. Lange. "Progesterone receptor action: defining a role in breast cancer." Expert review of endocrinology & metabolism 6.3 (2011): 359-369.
Denny, Wesley B., et al. "Structure-function analysis of squirrel monkey FK506-binding protein 51, a potent inhibitor of glucocorticoid receptor activity." Endocrinology 146.7 (2005): 3194-3201.
Feng, Xixi, et al. "Structure-affinity relationship analysis of selective FKBP51 ligands." Journal of medicinal chemistry 58.19 (2015): 7796-7806.

(Continued)

*Primary Examiner* — Samira J Jean-Louis
(74) *Attorney, Agent, or Firm* — Meunier Carlin & Curfman LLC

(57) ABSTRACT

The disclosure is directed to a method of enhancing progesterone receptor (PR) activity in a mammal, which comprises administering a composition comprising an inhibitor of FK506 binding protein 51 (FKBP51) to a mammal in need thereof, such as a pregnant human female, whereby progesterone receptor activity in the mammal is enhanced as compared to a mammal not administered the composition. The method results in an extension of the gestation period and a decreased likelihood of preterm birth and fetal growth restriction.

6 Claims, 21 Drawing Sheets

Specification includes a Sequence Listing.

(56) References Cited

OTHER PUBLICATIONS

Gaali, Steffen, et al. "Rapid, structure-based exploration of pipecolic acid amides as novel selective antagonists of the FK506-binding protein 51." Journal of medicinal chemistry 59.6 (2016): 2410-2422.
Gillespie, Charles F., and Charles B. Nemeroff. "Hypercortisolemia and depression." Psychosomatic medicine 67 (2005): S26-S28.
Gong, Shuai, et al. "Dynamics and correlation of serum cortisol and corticosterone under different physiological or stressful conditions in mice." PloS one 10.2 (2015): e117503.
Grimm, Sandra L., Sean M. Hartig, and Dean P. Edwards. "Progesterone receptor signaling mechanisms." Journal of molecular biology 428.19 (2016): 3831-3849.
Grundke-Iqbal, Inge, et al. "Intronic hormone microtubule-associated protein tau (tau) in Alzheimer cytoskeletal pathology." Proceedings of the National Academy of Sciences 83.13 (1986): 4913-4917.
Hartmann, Jakob, et al. "The involvement of FK506-binding protein 51 (FKBP5) in the behavioral and neuroendocrine effects of chronic social defeat stress." Neuropharmacology 62.1 (2012): 332-339.
Hubler, Tina R., and Jonathan G. Scammell. "Intronic hormone response elements mediate regulation of FKBP5 by progestins and glucocorticoids." Cell stress & chaperones 9.3 (2004): 243-52.
Jacobsen, Britta M., et al. "Expression profiling of human breast cancers and gene regulation by progesterone receptors." Journal of mammary gland biology and neoplasia 8.3 (2003): 257-268.
Kaikkonen, Sanna, et al. "Prostaglandin 15d-PGJ2 inhibits androgen receptor signaling in prostate cancer cells." Molecular Endocrinology 27.2 (2013): 212-223.
Klengel, Torsten, et al. "Allele-specific FKBP5 DNA demethylation mediates gene-childhood trauma interactions." Nature neuroscience 16.1 (2013): 33-41.
Lange, Carol A., et al. "Progesterone Receptor Action." Innovative Endocrinology of Cancer. Springer, New York, NY, 2008. 94-111.
Li, Xiaotao, and Bert W. O'Malley. "Unfolding the action of progesterone receptors." Journal of Biological Chemistry 278.41 (2003): 39261-39264.
Liu, Li, et al. "Global, regional, and national causes of under-5 mortality in 2000-15: an updated systematic analysis with implications for the Sustainable Development Goals." The Lancet 388. 10063 (2016): 3027-3035.
Migliaccio, Antimo, et al. "Activation of the Src/p21ras/Erk pathway by progesterone receptor via cross-talk with estrogen receptor." The EMBO journal 17.7 (1998): 2008-2018.
O'Leary et al., "A New Anti-Depressive Strategy for the Elderly: Ablation of FKBP5/FKBP51", PLoS One, 6: e248401-3 (2011).
Obr, Alison E., and Dean P. Edwards. "The biology of progesterone receptor in the normal mammary gland and in breast cancer." Molecular and cellular endocrinology 357.1-2 (2012): 4-17.
Owen, Gareth I., et al. "Progesterone regulates transcription of the p21 WAF1 cyclindependent kinase inhibitor gene through Sp1 and CBP/p300." Journal of Biological Chemistry 273.17 (1998): 10696-10701.
Proietti, Cecilia, et al. "Progestins induce transcriptional activation of signal transducer and activator of transcription 3 (Stat3) via a Jak-and Src-dependent mechanism in breast cancer cells." Molecular and cellular biology 25.12 (2005): 4826-4840.
Richer, Jennifer K., et al. "Differential gene regulation by the two progesterone receptor isoforms in human breast cancer cells." Journal of Biological Chemistry 277.7 (2002): 5209-5218.
Richer, Jennifer K., et al. "Convergence of Progesterone with Growth Factor and Cytokine Signaling in Breast Cancer Progesterone Receptors Regulate Signal Transducers and Activators of Transcription Expression and Activity." Journal of Biological Chemistry 273.47 (1998): 31317-31326.
Sabbagh, Jonathan J., et al. "Age-associated epigenetic upregulation of the FKBP5 gene selectively impairs stress resiliency." PLoS One 9.9 (2014): el07241.
Saitoh, Maki, et al. "Medroxyprogesterone acetate induces cell proliferation through up-regulation of cyclin D1 expression via phosphatidylinositol 3-kinase/Akt/nuclear factor-κB cascade in human breast cancer cells." Endocrinology 146.11 (2005): 4917-4925.
Sanchez, Edwin R. "Chaperoning steroidal physiology: lessons from mouse genetic models of Hsp90 and its cochaperones." Biochimica et Biophysica Acta (BBA)—Molecular Cell Research 1823.3 (2012): 722-729.
Tamm, Karin, et al. "Genes targeted by the estrogen and progesterone receptors in the human endometrial cell lines HEC1A and RL95-2." Reproductive Biology and Endocrinology 7.1 (2009): 150.
Tatro, Erick T., et al. "Modulation of glucocorticoid receptor nuclear translocation in neurons by immunophilins FKBP51 and FKBP52: implications for major depressive disorder." Brain research 1286 (2009): 1-12.
Tsai, Sophia Y., et al. "Molecular interactions of steroid hormone receptor with its enhancer element: evidence for receptor dimer formation." Cell 55.2 (1988): 361-369.
Tseng, Linda, et al. "Progesterone receptor (hPR) upregulates the fibronectin promoter activity in human decidual fibroblasts." DNA and cell biology 22.10 (2003): 633-640.
Wochnik, Gabriela M., et al. "FK506-binding proteins 51 and 52 differentially regulate dynein interaction and nuclear translocation of the glucocorticoid receptor in mammalian cells." Journal of Biological Chemistry 280.6 (2005): 4609-4616.
Yin, Ping, et al. "Genome-wide progesterone receptor binding: cell type-specific and shared mechanisms in T47D breast cancer cells and primary leiomyoma cells." PLoS one 7.1 (2012): e29021.
Zheng, Dali, et al. "MicroRNA-511 binds to FKBP5 mRNA, which encodes a chaperone protein, and regulates neuronal differentiation." Journal of Biological Chemistry 291.34 (2016): 17897-17906.
International Preliminary Report on Patentability issue for Application No. PCT/US2018/019505, dated Sep. 6, 2019.
International Search Report and Written Opinion in PCT/US2018/019505. dated May 15, 2018. 21 pages.
Hubler et al. , The FK506-Binding Immunophilin FKBP51 Is Transcriptionally Regulated by Progestin and Attenuates Progestin Responsiveness . Endocrinology. 2003, vol. 144(6), p. 2380-7 . Abstract; p. 2380, col. 1, para 1; p. 2381, col. 1, para 1, and col. 2, para 3; p. 2382, col. 2; p. 2384, col. 2, top para; and p. 2385, col. 2, and Fig 7 A.
Gaali et al. , Selective inhibitors of the FK506-binding protein 51 by induced fit. Nat Chem Biol. 2015, vol. 11 (1), p. 33-7. Entire documentation, especially Abstract.
Solano et al., Progesterone and HMOX-1 promote fetal growth by CD8+ T cell modulation. J Clin Invest. 2015, vol. 125(4), p. 1726-38. Entire documentation, especially Abstract.
Byrns, Regulation of progesterone signaling during pregnancy: implications for the use of progestins for the prevention of preterm birth. J Steroid Biochem Mol Biol. 2014, vol. 139, p. 173-81 . Entire documentation, especially Abstract; p. 174, Fig 1; and p. 175, Fig 2.
Nakagawa et al. , Immunosuppression with tacrolimus improved reproductive outcome of womenwith repeated implantation failure and elevated peripheral blood TH1/TH2 cellratios. Am J Re prod Immunol. 2015, vol. 73(4), p. 353-61 . Entire documentation, especially Abstract; p. 357, col. 1, lower para, col. 2, top para and middle para, and Table 1; and p. 359, col. 1, middle bara.
Schatz et al.; "Enhanced Human Decidual CelleExpressed FKBP51 May Promote Labor-Related Functional Progesterone Withdrawal"; The American Journal of Pathology, vol. 185, No. 9, dated Sep. 2015, 10 pages.

\* cited by examiner

Corticosterone serum levels on pregnancy day 11 within 30 min of 1st restrained stress (n=5/group).

Mean ± SE (N=5/group):

\* $p<0.05$ WT ST 194.07 ± 58.5 vs.
WT NS 23.03 ± 2.9

\*\* $p<0.05$ KO ST 160.22± 46.7 vs.
KO NS 28.75 ± 8.05

\* $p<0.05$ WT NS vs WT ST

\*\* $p<0.05$ KO NS vs KO ST

Mean ± SEM. \* $p<0.05$ vs. FKBP51+/+ non-stress mice; \*\* $p<0.05$ vs. FKBP51-/- non-stress mice

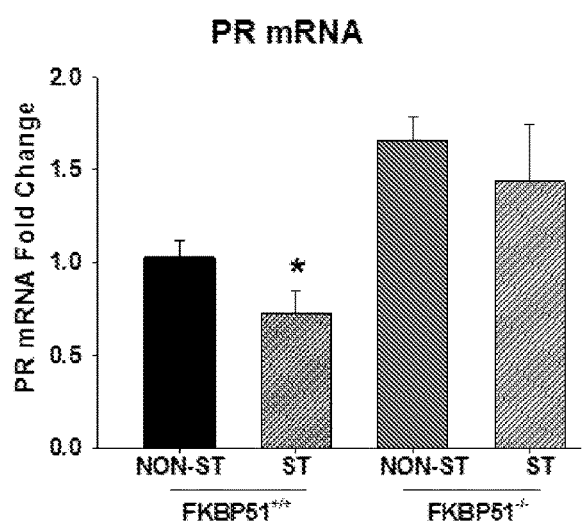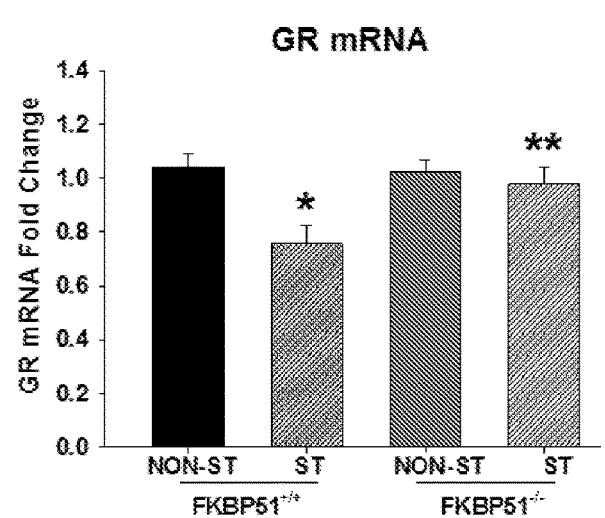
FIG. 13A                                FIG. 13B

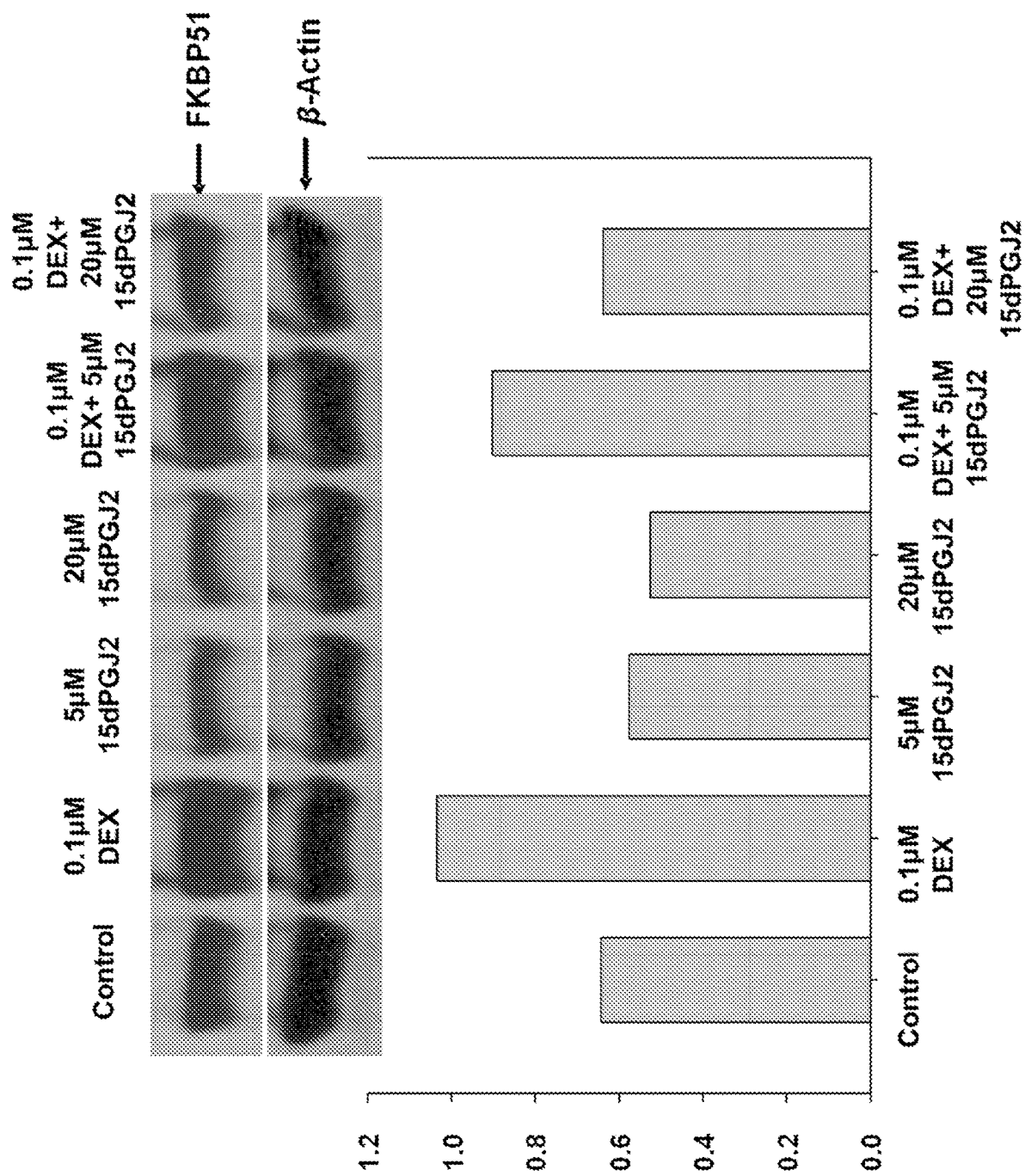

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
augccuuuug cucugcacuc a                                              21

US 11,197,868 B2

PREVENTION OF PRETERM BIRTH (PTB) BY INHIBITION OF FKBP51

CROSS-REFERENCE TO RELATED APPLICATION(S)

This application claims priority to U.S. Provisional Patent Application No. 62/463,430, filed on Feb. 24, 2017, which is incorporated herein by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 563 Byte ASCII (Text) file named "210112-9033-WO01-SEQ-LIST-02-23-18.txt," created on Feb. 23, 2018.

BACKGROUND

Preterm birth (PTB) is defined as birth prior to completion of 37 weeks of pregnancy. According to the U.S. Centers for Disease Control and Prevention (CDC), preterm birth rates decreased from 2007 to 2014, due in part to declines in the number of births to teens and young mothers. In 2016, however, preterm birth affected about 1 of every 10 infants born in the United States, and the preterm birth rate increased for the second straight year in 2016. Additionally, racial and ethnic differences in preterm birth rates remain. For example, in 2016 the rate of preterm birth among African-American women (14%) was about 50 percent higher than the rate of preterm birth among white women (9%). Worldwide, preterm birth is the leading cause of death for children under 5 years of age, and approximately 1 million children die each year due to complications of preterm birth (Liu et al., Lancet. 2016; 388(10063):3027-35; and Blencowe et al., The Lancet, June 2012. 9; 379(9832): 2162-72).

Infants born prematurely, especially prior to 32 weeks, have higher rates of death and disability, including, for example, breathing problems, feeding difficulties, cerebral palsy, developmental delays, vision problems, and hearing problems. In 2015, preterm birth and low birth weight accounted for about 17% of infant deaths. Preterm births also exert extreme psychological and financial tolls on affected families.

Interventions that help reduce the risk of preterm birth include quitting smoking, avoiding drugs and alcohol, and obtaining early and consistent prenatal care. Preventing preterm birth remains a challenge because there are many causes of preterm birth, and such causes are complex and not always well understood. Thus, there remains a need for improved methods for preventing preterm birth in humans.

BRIEF SUMMARY OF THE INVENTION

The disclosure provides a method of enhancing progesterone receptor (PR) activity in a mammal, which comprises administering a composition comprising an inhibitor of FK506 binding protein 51 (FKBP51) to a mammal in need thereof, whereby progesterone receptor activity in the mammal is enhanced as compared to a mammal not administered the composition.

The disclosure also provides a method of extending the gestation period of a mammal, which comprises administering a composition comprising an inhibitor of FK506 binding protein 51 (FKBP51) to a pregnant mammal, whereby the gestation period of the pregnant mammal is extended as compared to a mammal that is not administered the composition.

The disclosure further provides a method of preventing fetal growth restriction in a mammal comprising administering a composition comprising an inhibitor of FK506 binding protein 51 (FKBP51) to a pregnant mammal, whereby fetal growth restriction is prevented as compared to a mammal that is not administered the composition.

BRIEF DESCRIPTION OF THE SEVERAL VIEWS OF THE DRAWING(S)

FIGS. 13A and 13B are graphs showing placental PR (FIG. 13A) and glucocorticoid receptor (GR) (FIG. 13B) gene expression in WT and KO mice on GD18.25.

FIGS. 15A and 15B are an image showing an immunoblot (15A) and a graph (15B) showing the effect of DEX (0.1 μM) or 15dPGJ2 (5 or 20 μM) or DEX+15dPGJ2 on FKBP51 expression in primary term DC cultures.

DETAILED DESCRIPTION OF THE INVENTION

Figure 1:
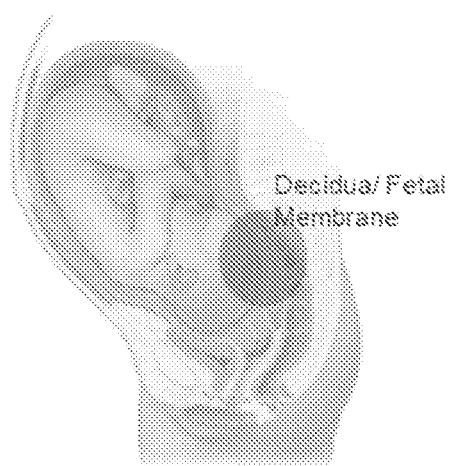
FIG. 1 is a schematic diagram which shows dysregulation of decidual cell progesterone receptor activity in the pathogenesis of preterm birth.

The present disclosure is predicated, at least in part, on the discovery that inhibiting the activity of the FK506 binding protein 51 (FKBP51) in mice enhances progesterone receptor-mediated transcription, which leads to prevention of preterm birth and extension of the gestation period. The present disclose is further predicated on the discovery that inhibiting the activity of FKBP51 leads to the prevention of fetal growth restriction (FGR), also referred to as intrauterine growth restriction. Thus, the disclosure provides a method of enhancing progesterone receptor (PR) activity in a mammal, which comprises administering a composition comprising an inhibitor of FK506 binding protein 51 (FKBP51) to a mammal in need thereof, such as a pregnant human female. Enhanced PR activity results in extension of the gestation period of a pregnant mammal and prevents preterm birth.

Progesterone receptors (PRs) are ligand-activated transcription factors that are members of the steroid hormone receptor (SR) subfamily of nuclear receptors. Two common isoforms (A and B) are expressed from the same gene via alternate translational start sites: PR-B refers to the full-length receptor, while PR-A is an N-terminally truncated version which lacks the first 164 amino acids found in PR-B. The PR gene is differentially regulated by two independent (isoform-specific) promoters. The A and B isoforms can act as homo-(A:A or B:B) or heterodimers (A:B) and are capable of binding DNA at progesterone response elements and/or via tethering to other transcription factors (e.g., signal transducers and activators of transcription (STATs), specificity protein 1 (SP1), and activator protein 1) (see, e.g., Tsai et al., *Cell*, 55(2): 361-369 (1988); Richer et al., *J. Biol. Chem.*, 273(47): 31317-31326 (1998); Owen et al., *J. Biol. Chem.*, 273(17): 10696-10701 (1998); Proietti et al., *Mol Cell Biol.*, 25(12): 4826-4840 (2005); and Tseng et al., *DNA Cell Biol*, 22(10): 633-640 (2003)). PR-A and -B can regulate the same or different (isoform-specific) sets of target genes and exhibit both ligand-dependent and -independent activities (Jacobsen et al., *J. Mammary Gland Biol Neoplasia*, 8(3): 257-268 (2003); and Richer et al., *J. Biol. Chem.*, 277(7):5209-5218 (2002)); these PR functions are heavily influenced by cross-talk/input from peptide growth factor-initiated signal transduction pathways (Lange et al., *Adv. Exp. Med. Biol.*, 630: 94-111 (2008)). A third putative PR isoform, known as PR-C, is truncated still further downstream by use of an additional AUG codon within the DNA-binding domain; this highly tissue-specific receptor inhibits the actions of PR-B in the uterus and is important for the induction of labor (Condon et al., *Mol. Endocrinol.*, 20(4): 764-775 (2006)).

Several genes whose expression is regulated by PRs have been identified. For example, several PR-regulated genes are involved in regulation of transcription and cell differentiation, including, but not limited to, TSC-22, a putative transcription factor, CD-9/MRP-1 (motility-related protein 1), Na+/K+-ATPase α1, desmoplakin, CD-59/protectin, and FKBP51, an immunophilin. Other large scale investigations have demonstrated that PR-A and PR-B regulate different subsets of genes involved in particular functional pathways (Richer et al., *J. Biol. Chem.*, 277: 5209-5218 (2002)). In breast cancer cells, although some genes are regulated by progesterone through both PR isoforms, most genes are uniquely regulated through one or the other isoform, predominantly through PR-B. A subset of these genes is involved in breast cancer and mammary gland development, including, for example, STAT5A, MSX-2, and C/EBPβ. A large number of PR-regulated genes are involved in membrane-initiated events, including proteins involved in cell adhesion, membrane-bound receptors, calcium-binding proteins, and signaling molecules, and these genes represent almost half of all progesterone-regulated genes identified in breast cancer cell models. PRs also have been shown to regulate transcription of genes involved in metabolism, such as cholesterol/steroid, fatty acid, nucleotide, or amino acid metabolism. Progesterone-regulated (up- or downregulated) genes in PR-A-positive Ishikawa cells, include, for example, retinoic acid receptor γ, integrin β4/α7, mitogen-activated protein kinase P97, p16-INK4, cytokeratin 8, and cyclin D1. In contrast, Ishikawa cells expressing PR-B exhibited downregulation of three genes: IGFBP-3, fibronectin, and replication protein A, suggesting cell- and tissue-specific distinctions in target gene regulation between the two PR isoforms. Other PR target genes have functions in transcription, cell growth, and protein processing, indicating a broad range of genes regulated by PRs (Li, X., and B. W. O'Malley, *J. Biol. Chem.*, 278: 39261-39264 (2003)).

PRs function not only as critical regulators of transcription but also to activate signal transduction pathways, many of which are involved in pro-proliferative signaling in the breast. In this regard, in vitro data suggest that PR extranuclear actions lead to rapid activation of protein kinases (e.g., MAPK, PI3K/Akt and c-Src) in part by a ligand-induced interaction between PR and c-Src kinase (see, e.g., Migliaccio et al., *EMBO J*, 17(7): 2008-2018 (1998); Boonyaratanakornkit et al., *Mol Cell.*, 8(2): 269-280 (2001); and Saitoh et al., *Endocrinology*, 146(11): 4917-4925 (2005)). In addition, PR-B, but not PR-A, and estrogen receptor-α have been shown to participate in membrane-tethered protein complexes capable of rapidly activating c-Src and MAPKs. Although the rapid signaling actions of PRs take place independently of transcription (i.e., in seconds to minutes), membrane-initiated and nuclear functions of PRs are fully integrated events (Daniel et al., *Expert Rev. Endocrinol. Metab.*, 6(3): 359-369 (2011)). The methods described herein may be used to enhance the activity of any PR isoform (i.e., PR-A, PR-B, and/or PR-C).

The methods described herein involve enhancing progesterone receptor (PR) activity in a mammal comprising administering a composition comprising an inhibitor of FK506 binding protein 51 (FKBP51) to a mammal in need thereof. FKBP51 is an Hsp90 co-chaperone that helps regulate the function of specific Hsp90 clients, such as the glucocorticoid receptor (GR) (Denny et al., *Endocrinology*, 146: 3194-3201 (2005)) and the microtubule-associated protein Tau. FKBP51 is dysregulated in several diseases, but its functional regulation is not well-understood. FKBP51 inhibits GR function, leading to delayed hypothalamic-pituitary-adrenal axis feedback and elevated circulating glucocorticoid levels (O'Leary et al., *PLoS One*, 6: e248401-3 (2011); Wochnik et al., *J. Biol. Chem.*, 280: 4609-4616 (2005); and Denny et al., supra), a phenomenon observed in major depression (Gillespie C. F. and Nemeroff C. B., *Psychosom. Med.*, 67: S26-S28 (2005)). Indeed, single nucleotide polymorphisms in the FKBP51 gene have been associated with increased risk for depression, as well as other neuropsychiatric disorders including post-traumatic stress disorder (PTSD) (Binder et al., *Nat. Genet.*, 36: 1319-1325 (2004); Binder et al., *JAMA*, 299: 1291-1305 (2008); and Klengel et al., *Nat. Neurosci.*, 16: 33-41 (2013)). Mice with a targeted deletion of Fkbp51 display resilience to stress and accelerated hypothalamic-pituitary-adrenal axis reactivity (Sabbagh et al., *PLoS One*, 9: e107241 (2014); and Hartmann et al., *Neuropharmacology*, 62: 332-339 (2012)). FKBP51 expression is also increased in Alzheimer disease (AD), which is characterized by accumulation of misfolded Tau (Grundke-Iqbal et al., *Proc. Natl. Acad. Sci. U.S.A.*, 83: 4913-4917 (1986)). FKBP51 has been shown to accelerate Tau oligomerization and neurotoxicity in vitro and in vivo, suggesting that it may be contributing to the pathogenesis of AD (Blair et al., *J. Clin. Invest.*, 123: 4158-4169 (2013)). The FKBP51 promoter region and introns contain several progesterone or glucocorticoid response elements (PREs or GREs), which mediate transcriptional induction of FKBP51 by progesterone receptor (PR) and/or glucocorticoid receptor (GR) (Hubler T R, Scammell J G., *Cell Stress & Chaperones*, 9(3): 243-52 (2004)). In turn, elevated levels of FKBP51 can inhibit transcriptional activity of both PR and GR (Hubler et al., *Endocrinology*, 144(6): 2380-7 (2003); Sanchez, E. R., *Biochimica et Biophysica Acta.*, 1823(3): 722-9 (2012); and Tatro et al., *Brain Research*, 1286: 1-12 (2009)). The present disclosure also demonstrates that FKBP51 acts as a repressor of progesterone receptor (PR) mediated transcription.

Any suitable PR activity may be enhanced by the methods disclosed herein. In one embodiment, the PR activity may be one or more PR-mediated signaling pathways, i.e., any series of molecular signals generated as a consequence of a progesterone binding to a progesterone receptor. For example, the disclosed method may enhance the activity of Src/MAPK signaling that is induced by progesterone binding to PR (Boonyaratanakornkit et al., *Steroids*, 73(9-10): 922-928 (2008)). PR-mediated signaling pathways are further described in, e.g., Grimm et al., *J. Mol. Biol.*, 428(19): 3831-49 (2016); and Obr A., Edwards D. P., *Molecular and Cellular Endocrinology*, 357(1-2): 4-17 (2012). In another embodiment, the PR activity may be PR-mediated gene transcription. The disclosed method may enhance the transcription or expression of any gene that is regulated by progesterone binding to a progesterone receptor, such as any of the genes described herein, or genes disclosed in, e.g., Tamm et al., *Reprod Biol Endocrinol.*, 7: 150 (2009); and Yin et al., *PLoS One*, 7(1): e29021 (2012).

In accordance with the methods described herein, progesterone receptor activity in the mammal may be enhanced (e.g., improved or increased) to any suitable degree as compared to a mammal not administered the composition comprising an inhibitor of FKBP51. In one embodiment, PR activity may be enhanced by at least about 5% as compared to a mammal not administered the composition (e.g., 10%, 20%, 30%, 40%, 50%, 60%, 70%, 80%, 90%, 100%, 200% or higher). In another embodiment, PR activity may be enhanced at least about 25% as compared to a mammal not administered the composition (e.g., 35%, 45%, 55%, 65%, 75%, 85%, 95%, 125% or higher). In other embodiments, PR activity may be enhanced at least about 50% as compared to a mammal not administered the composition, or at least about 100% as compared to a mammal not administered the composition.

Enhancement in PR-mediated signaling activity may be measured using any suitable method known in the art. Similarly, PR-mediated gene transcription may be measured using routine methods known in the art such as, for example, Northern blot, quantitative PCR, reverse transcriptase PCR (RT-PCR), microarray analysis, serial analysis of gene expression (SAGE), RNA sequencing (RNA-Seq), and techniques described in, e.g., Green, M. and J. Sambrook (eds.), *Molecular Cloning: A Laboratory Manual*, 4$^{th}$ Edition, Cold Spring Harbor Laboratory Press (2012).

The term "inhibitor of FK506 binding protein 51 (FKBP51)," as used herein, refers to any molecule, compound, or substance that prevents, blocks, or impairs the function or activity of FKBP51. For example, an FKBP51 inhibitor may prevent or block expression of the gene encoding FKBP51. Alternatively, an FKBP51 inhibitor may prevent or block production of the FKBP51 protein following gene expression. In other embodiments, an FKBP51 inhibitor may prevent, block, or impair a function of the FKBP51 protein (e.g., inhibition of glucocorticoid receptor function). Any suitable inhibitor of FKBP51 may be used in the methods described herein. Suitable FKBP51 inhibitors include, but are not limited to, non-coding RNA (i.e., RNA that does not encode protein), such as small interfering RNAs (siRNAs), microRNAs (miRNAs), and short hairpin RNAs (shRNAs). siRNAs and miRNAs are central to RNA interference (RNAi), which is a biological process in which RNA molecules inhibit gene expression or translation by neutralizing targeted mRNA molecules. siRNA, also known as short interfering RNA or silencing RNA, is a class of double-stranded RNA molecules 20-25 base pairs in length, which interferes with the expression of specific genes with complementary nucleotide sequences by degrading mRNA after transcription, preventing translation (Agrawal et al., *Microbiol. Mol. Biol. Rev.*, 67(4): 657-668 (2003). shRNAs are artificial RNA molecules with a tight hairpin turn that can be used to silence target gene expression via RNAi. miRNAs are small non-coding RNA molecules about 22 base pairs in length, which are found in plants, animals, and some viruses and function in RNA silencing and post-transcriptional regulation of gene expression (see, e.g., Ambros, V., *Nature*, 431 (7006): 350-355 (2004); and Bartel, D. P., *Cell*, 116(2): 281-297 (2004)). While the majority of miRNAs are located within a cell, some miRNAs, commonly known as circulating miRNAs or extracellular miRNAs, have also been found in extracellular environment, including various biological fluids and cell culture media. miRNAs differ from siRNAs in that miRNAs are derived from regions of RNA transcripts that fold back on themselves to form short hairpins, whereas siRNAs derive from longer regions of double-stranded RNA. In one embodiment, the FKBP51 inhibitor is a miRNA comprising the nucleic acid sequence of AUGCCUUUUGCUCUGCA-CUCA (SEQ ID NO: 1), which is also referred to as miR-511 (described in Zheng et al., *J. Biol. Chem.*, 291(34): 17897-17906 (2016)).

Other FKBP51 inhibitors include, but are not limited to, tacrolimus, selective antagonist of FKBP51 by induced fit 1 (SAFit1), SAFit2, a pipecolic acid amide, and 15-deoxy-Δ12,14-prostaglandin J2. Tacrolimus (marketed as PROGRAF®, ADVAGRAF®, and PROTOPIC®) is a macrolide immunosuppressant produced by *Streptomyces tsukubaensis*, which is indicated for the prophylaxis of organ rejection in patients receiving allogeneic liver, kidney, or heart transplants. Tacrolimus inhibits T-lymphocyte activation by first binding to the immunophilin FK506 binding protein-12 (FKBP-12). A complex of tacrolimus-FKBP-12, calcium, calmodulin, and calcineurin is then formed and the phosphatase activity of calcineurin is inhibited. This prevents the dephosphorylation and translocation of nuclear factor of activated T-cells (NF-AT), a nuclear component thought to initiate gene transcription for the formation of lymphokines. Tacrolimus also inhibits the transcription of genes encoding IL-3, IL-4, IL-5, GM-CSF, and TNF-α, all of which are involved in the early stages of T-cell activation.

SAFit1 and SAFit2 are highly selective small molecule inhibitors of FKBP51, which achieve selectivity for FKBP51 by an induced-fit mechanism (Gaali et al., *Nature Chemical Biology*, 11: 33-39 (2015)). The FKBP51 inhibitor may also include analogs or derivatives of SAFit1 and SAFit2, such as the compounds modified at the C9 cyclohexyl group described in Gaali et al., *J. Med. Chem.*, 58: 7796-7806 (2015). In another embodiment, the FKBP51 inhibitor may be a pipecolic acid amide compound, such as a pipecolic acid derivative of SAFit1, in which the potentially labile pipecolic ester group is replaced by a low molecular weight amide. Such pipecolic acid amide derivatives are described in Gaali et al., *J. Med. Chem.*, 59: 2410-2422 2016, and have lower molecular weights without affecting FKBP51 selectivity.

The methods described herein involve decreasing FKBP51 expression in a mammal comprising administering a composition comprising 15-deoxy-Δ12,14-prostaglandin J2 (15d-PGJ2) to a mammal in need thereof. The compound 15-deoxy-Δ12,14-prostaglandin J2 is an endogenously produced anti-inflammatory prostaglandin which has been shown to target the androgen receptor (AR) and acts as a potent AR inhibitor, rapidly repressing AR target genes, such as FKBP51 and TMPRSS2, in prostate cancer cells (Kaikkonen et al., *Mol Endocrinol*, 27(2): 212-223 (2013)). As demonstrated herein, 15dPGJ2 may completely block glucocorticoid (e.g., dexamethasone (DEX)) induced FKBP51 expression. 15dPGJ2 and its derivatives may be used in methods to prevent preterm birth and fetal growth restriction.

It will be appreciated that the FKBP51 inhibitor may include other inhibitors known in the art, as well as inhibitors that have not yet been identified.

As demonstrated herein, inhibiting the activity of FKBP51 enhances PR activity and decreases the production of prostaglandins and proteases associated with uterine contractions and cervical change in mammals, which delays or prevents preterm birth (PTB) by extending the gestation period of the mammal. Thus, the disclosure also provides a method of extending the gestation period of a mammal comprising administering a composition comprising an inhibitor of FKBP51 to a pregnant mammal, whereby the gestation period of the pregnant mammal is extended as compared to a mammal that is not administered the composition. The disclosure also demonstrates that reducing or blocking the expression of FKBP51 prevents fetal growth restriction. Thus, the disclosure also provides a method of preventing fetal growth restriction comprising administering a composition comprising an inhibitor of FKBP51 to a pregnant mammal, whereby fetal growth restriction is prevented as compared to a mammal that is not administered the composition. Descriptions of the FKBP51 inhibitor and progesterone receptor activity, and components thereof, set forth above in connection with other embodiments of the disclosure also are applicable to those same aspects of the aforesaid method of extending the gestation period and method of preventing fetal growth restriction.

The term "gestation period," as used herein, refers to the time period for fetal development from conception until birth. The average gestation period for a variety of mammals is known in the art. Humans, for example, have a gestation period of 40 weeks from a last menstrual period or 38 weeks from conception, while the gestation period for mice is typically about three weeks. The disclosed method desirably "extends" the gestation period of a pregnant mammal if childbirth is not pre- or early-term, i.e., the date of childbirth is full term, late term, or postterm. With respect to human pregnancies, the terms "preterm birth" (PTB) and "early term birth" are used interchangeably herein and refer to childbirth prior to completion of 37 weeks and 39 weeks of pregnancy, respectively. Preterm birth may be further categorized as "late" preterm (i.e., birth between 34 and 36 completed weeks of pregnancy), "moderately" preterm (i.e., birth between 32 and 34 weeks of pregnancy), "very" preterm (i.e., birth at less than 32 weeks of pregnancy), or "extremely" preterm (i.e., birth before 28 weeks of pregnancy). The majority of preterm births occur in the late preterm stage. In contrast, in a "full term" pregnancy, childbirth occurs between 39 and 40 weeks of pregnancy. In a "late term" pregnancy, childbirth occurs during week 41 of pregnancy, and in a "postterm" pregnancy, childbirth occurs at 42 weeks of pregnancy or beyond.

The terms "fetal growth restriction" and "intrauterine growth restriction" are synonymous and refer to a condition in which a fetus is smaller than expected for the number of weeks of pregnancy (gestational age). The weight of a fetus is often described in terms of an estimated weight less than the 10th percentile. Newborn babies with fetal growth restriction may be called "small for gestational age." The inhibition of FKBP51 may completely block or reduce glucocorticoid-induced FKBP51 gene expression, such as expression induced by the glucocorticoids dexamethasone (DEX) and medroxyprogesterone acetate.

The disclosed methods reduce the likelihood of, and desirably prevent, preterm birth (PTB) in a pregnant mammal as compared to a mammal not administered the composition. The disclosed methods reduce the likelihood of, and desirably prevent, fetal growth restriction in a pregnant mammal as compared to a mammal not administered the composition. Thus, the disclosed methods comprise administering a "therapeutically effective amount" of the FKBP51 inhibitor. A "therapeutically effective amount" refers to an amount effective, at dosages and for periods of time necessary, to achieve a desired therapeutic result (e.g., extension of gestation period). The therapeutically effective amount may vary according to factors such as the condition or disease being treated, age, sex, and weight of the mammal, and the ability of the FKBP51 inhibitor to elicit a desired response in the individual. Alternatively, the pharmacologic and/or physiologic effect may be prophylactic, i.e., the effect completely or partially prevents a condition, disease, or symptom thereof. In this respect, the disclosed method comprises administering a "prophylactically effective amount" of the FKBP51 inhibitor. A "prophylactically effective amount" refers to an amount effective, at dosages and for periods of time necessary, to achieve a desired prophylactic result (e.g., prevention of preterm birth and/or fetal growth restriction).

In one embodiment, a therapeutically or prophylactically effective amount of an FKBP51 inhibitor is administered to a mammal in the form of composition comprising the FKBP51 inhibitor and a carrier (e.g., a pharmaceutically acceptable carrier). The composition may be administered to any mammal (e.g., a human, non-human primate, rodent, dog, cat, whale, etc.), and is desirably administered to a female mammal. In one embodiment, the mammal is a pregnant female mammal, such as a pregnant human female. The composition desirably is a physiologically acceptable (e.g., pharmaceutically acceptable) composition, which comprises a carrier, preferably a physiologically (e.g., pharmaceutically) acceptable carrier, and the therapeutically or prophylactically effective amount of the FKBP51 inhibitor. Any suitable carrier can be used within the context of the disclosure, and such carriers are well known in the art. The choice of carrier will be determined, in part, by the particular use of the composition (e.g., administration to a mammal) and the particular method used to administer the composition. The composition optionally can be sterile. The composition can be frozen or lyophilized for storage and reconstituted in a suitable sterile carrier prior to use. Suitable compositions include aqueous and non-aqueous isotonic sterile solutions, which can contain anti-oxidants, buffers, suspending agents, solubilizers, thickening agents, stabilizers, and/or preservatives. The compositions can be generated in accordance with conventional techniques described in, e.g., Remington: *The Science and Practice of Pharmacy*, 21st Edition, Lippincott Williams & Wilkins, Philadelphia, Pa. (2001).

The composition may comprise any suitable dose of the FKBP51 inhibitor. A suitable dose will be determined, at least in part, by the specific type of FKBP51 inhibitor, a particular use of the FKBP51 inhibitor (e.g., prevention of preterm birth or fetal growth restriction), and the particular method used to administer the composition. Therapeutic efficacy can be monitored by periodic assessment of treated patients. For repeated administrations over several days or longer, depending on the condition, the treatment can be repeated until a desired outcome occurs. However, other dosage regimens may be useful and are within the scope of the disclosure.

The composition can be administered to a mammal (e.g., a human) using standard administration techniques, including oral, intravenous, intraperitoneal, subcutaneous, pulmonary, transdermal, intramuscular, intranasal, buccal, sublingual, rectal, vaginal, or suppository administration. The FKBP51 inhibitor may be administered alone or in combination with other drugs or therapies for extension of the gestation period, prevention of preterm birth, and/or fetal growth restriction. For example, the disclosed methods may be performed in conjunction with the administration of progesterone supplements and/or cervical cerclage, which is a surgical procedure performed during pregnancy in women with a short cervix, or a history of cervical shortening that resulted in a preterm birth.

The following examples further illustrate the invention but, of course, should not be construed as in any way limiting its scope.

Example 1

This example demonstrates the expression pattern of FKBP51 in mice and the effects of FKBP51 regulation on preterm birth (PTB) in mice.

Figure 2:
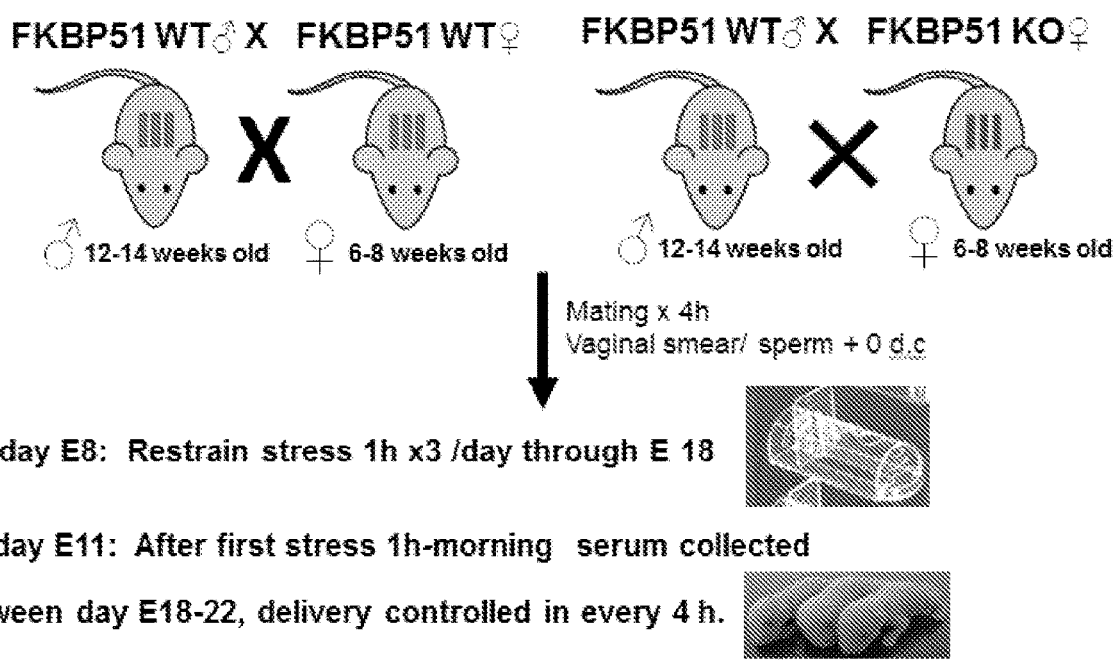
FIG. 2 is a diagram showing the design of experiments to examine the role of FKBP51 in stress-induced PTB using FKBP51−/− mice.
Figure 3:
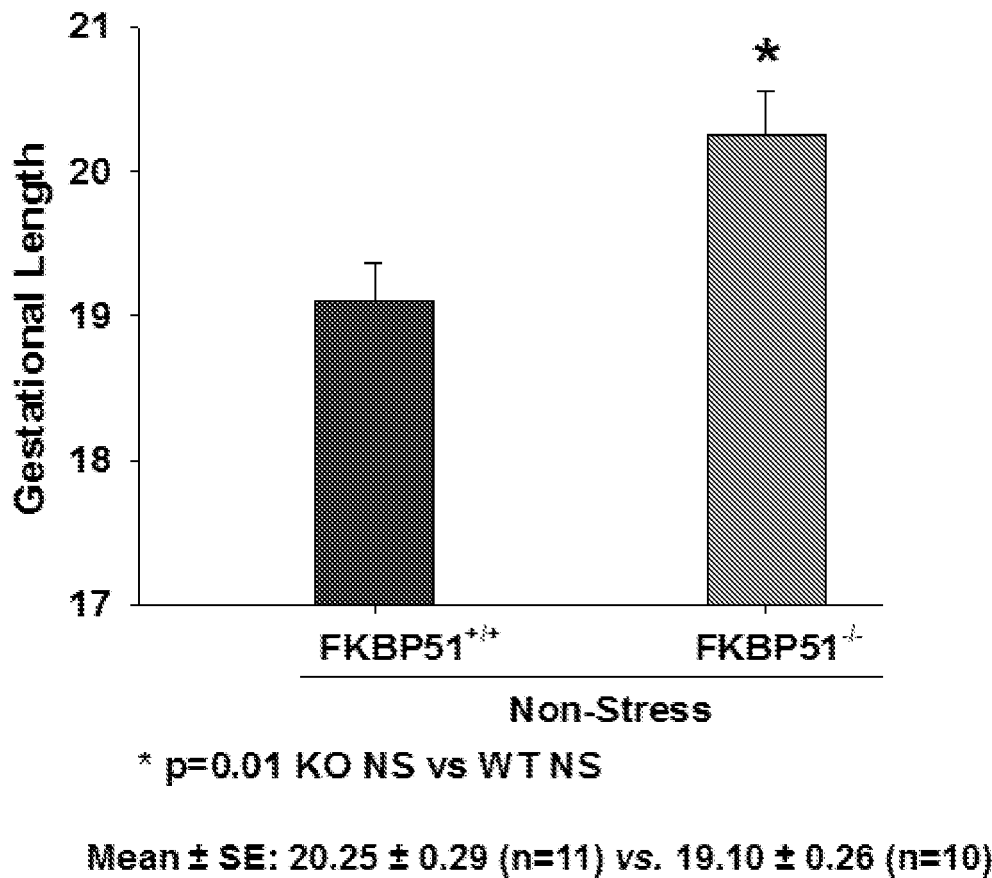
FIG. 3 is a graph showing prolonged gestation in non-stressed FKBP51−/− vs FKBP51+/+ mice.
Figure 4:
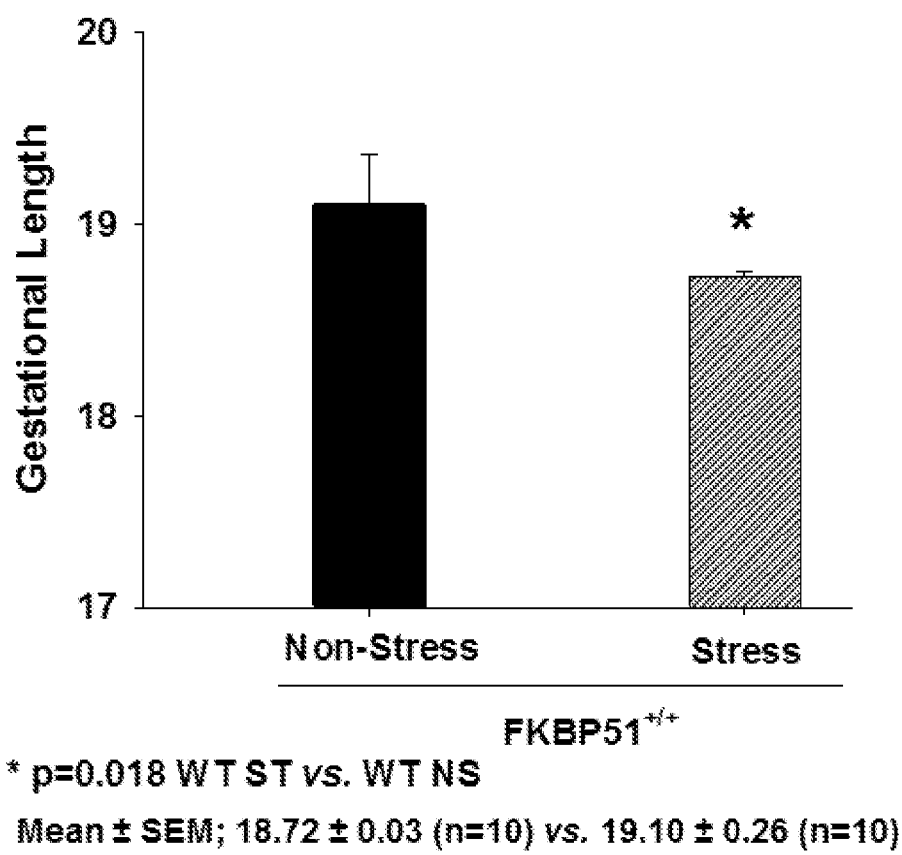
FIG. 4 is a graph showing that prenatal stress induces PTB in wild type (WT) mice.
Figure 5:
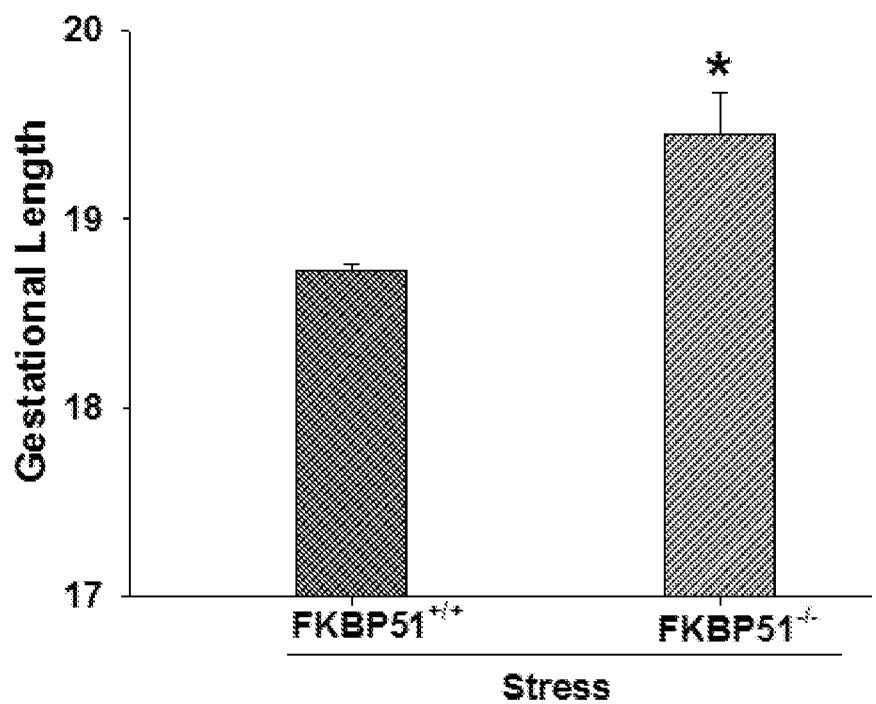
FIG. 5 is a graph showing that gestational length is significantly longer in stress induced FKBP51 KO vs. WT mice.

FKBP51-knockout (KO; FKBP51-/-) and wild type (WT) animals mice (provided by Chad Dickey, PhD; USF Health Morsani College of Medicine) were used to analyze FKBP51 expression and test the hypothesis that FKBP51 regulates preterm birth in mice. To define the role of FKBP51 on birth timing, the gestational length was compared in pregnancies from WT or FKBP51 KO mice mated with WT male littermates (see FIG. 2). This analysis revealed significantly prolonged gestation (more than one day) in KO female mice compared to WT female mice, as shown in FIG. 3, providing the first evidence that FKBP51 regulates gestational length. Moreover, compared to the gestational length in non-stress WT controls, restrained stress significantly reduced gestational length in the stressed WT group (19.10 day vs. 18.72, P=0.018), as shown in FIG. 4, suggesting that gestational stress induces preterm birth (PTB). The impact of FKBP51 on gestational length in stress-induced PTB is unknown. The FKBP51 gene knockout approach described above uncovered significantly longer gestational length in stressed FKBP51 KO mice mated with WT male littermates versus stressed WT mice mated with WT male littermates, as shown in FIG. 5. The results indicate that the absence of FKBP51 prevents stress-induced PTB.

Figure 6:
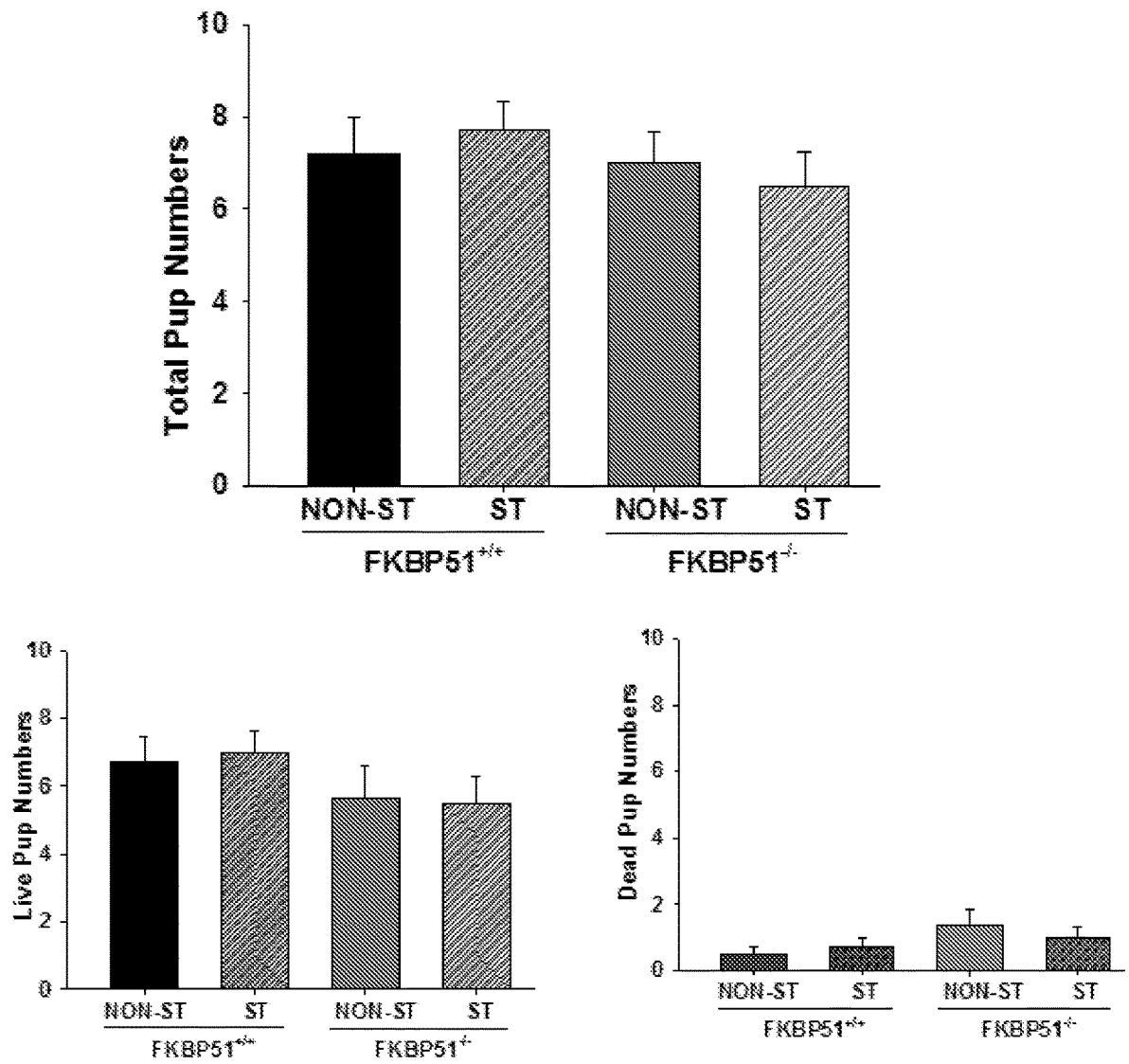
FIG. 6 is a series of graphs showing that there is no difference in pup numbers among all groups of stressed and non-stressed FKBP51−/− and FKBP51+/+ mice.

The number of pups born to WT or FKBP51 KO mice mated with WT males also was examined. The average pup numbers at birth or surviving pups at postnatal day 1 did not differ significantly among all four groups, as shown in FIG. 6. The number of dead pups from KO mothers were slightly higher, but did not attain statistical significance compared to pups from WT mothers. Moreover, the dead pups exhibited no apparent malformations. The sex ratio of the pups was approximately 1:1 in all groups.

Figure 7:
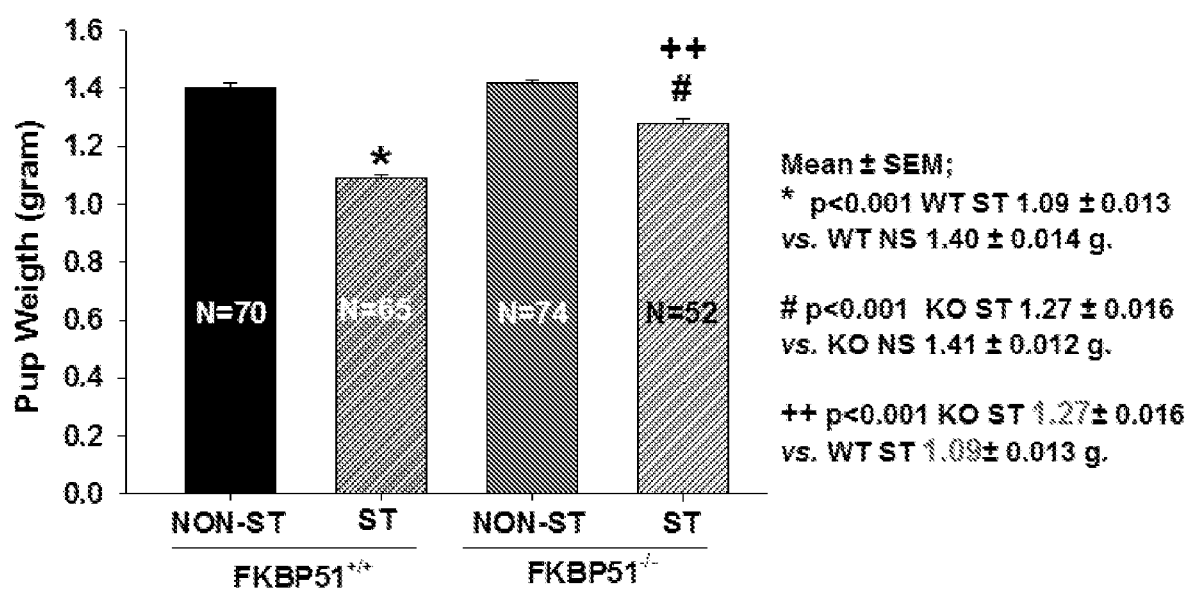
FIG. 7 is a graph showing that stress induction causes pups to be born with lower body weight.

To define the consequences of maternal knockdown of FKBP51 expression on stress-induced fetal growth restriction during pregnancy, weights of pups delivered from WT or FKBP51 KO pregnancies were compared. Pup weights in all non-stressed groups (FKBP51+/+xFKBP51+/+ or FKBP51-/-x FKBP51+/+ mated mice) were similar, as shown in FIG. 7. However, restrained stress induced a significant reduction in pup weights in either FKBP51+/+ xFKBP51+/+ or FKBP51-/-x FKBP51+/+ mice. Specifically, pup weights were reduced by 22% in FKBP51+/+-stressed versus non-stressed FKBP51+/+ mice, whereas this stressed-induced reduction in pup weight regressed to 10% in FKBP51-/- mice. These results indicate that pregnancies characterized by knockdown of maternal FKBP51 expression alone significantly nullifies stress-induced FGR (FKBP51-/-vs. FKBP51+/+ mice 10% versus 22% stress-induced reduction in birth weights, respectively).

Figure 8:
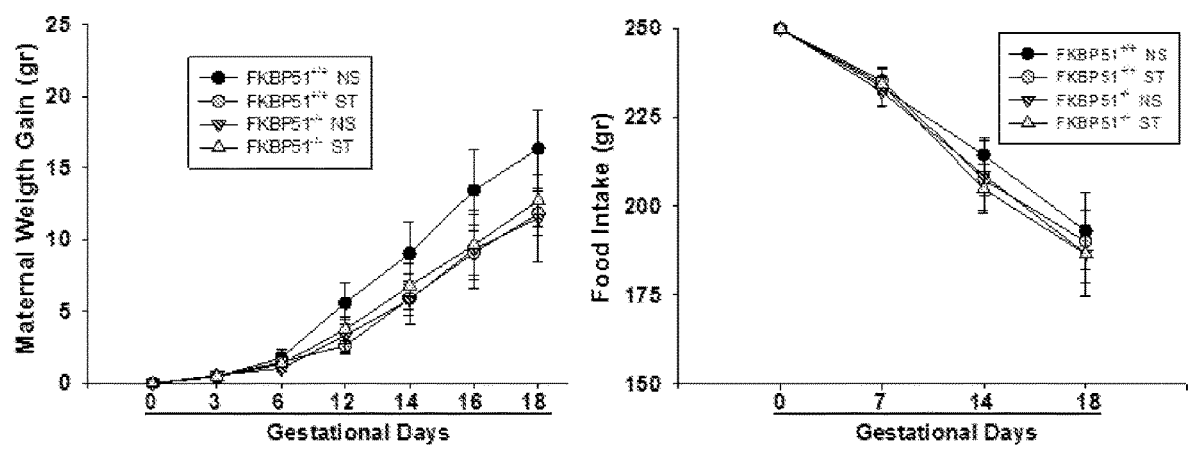
FIG. 8 is a series of graphs showing similar maternal body weight gain and food intake during pregnancy in stressed and non-stressed mice.

Pregnant mice were weighed at 3 day intervals from gestational day (GD) GD0 to GD18 to determine whether maternal deletion of FKBP51 or restrained stress affects gestational weight gain. To determine whether restrained stress impacts food and water intake, the remaining amounts of food and water were measured every week and subtracted from the initial amount (250 g food and 250 ml water). These analyses revealed no significant differences for gestational weight gain or food or water intake among all four groups, as shown in FIG. 8.

Taken together, these results provide strong evidence for therapeutic use of FKBP51 inhibitors against prematurity.

Example 2

This example describes experiments comparing corticosterone levels in stressed vs. non-stressed mice.

Figure 9:
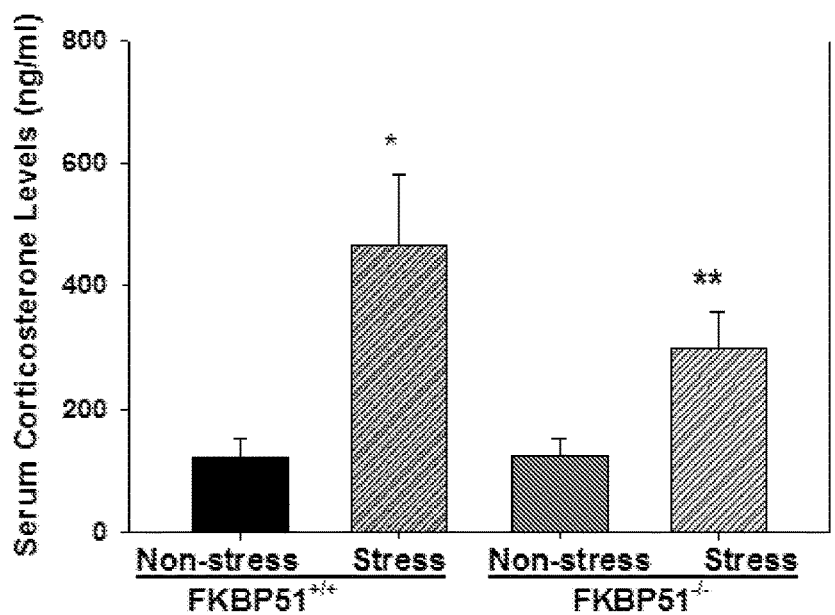
FIG. 9 is a graph showing elevated cortisol levels in stressed vs. non-stressed mice.

In rodents, plasma corticosterone is considered to be the main glucocorticoid involved in regulating stress responses, and the presence of plasma cortisol in serum also has been confirmed in rodents (Gong et al., *PLoS One*, 10: e0117503 (2015)). The dynamics of mouse serum cortisol and corticosterone may be closely correlated under different physiological or stress conditions, and corticosterone may be a better adaptation-related biomarker than cortisol during chronic stress, whereas cortisol may be a quicker responder than corticosterone during severe acute stress. Therefore, serum corticosterone levels were analyzed in samples obtained from mice tested in Example 1. Blood sampling was performed at 10 to 11 am on gestation days (GDs) 11 after the first stress exposure in WT and KO mice and in non-stressed (control) groups. A commercially available enzyme-linked immunosorbent assay (ELISA) kit was used to quantify serum corticosterone levels. The results are shown in FIG. 9, and confirm that restrained stress significantly induces maternal serum corticosterone levels in both WT and KO mice.

Example 3

This example demonstrates the effect of maternal and fetal genotype in stress-induced preterm birth (PTB).

Figure 16:
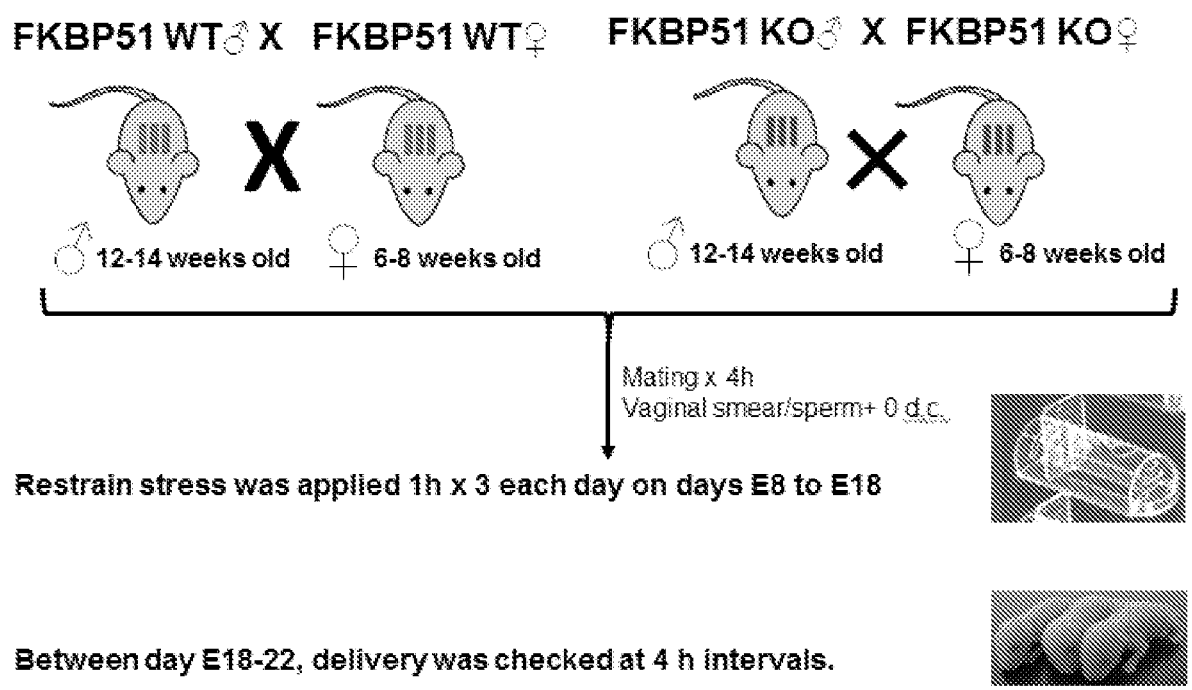
FIG. 16 is a diagram showing the effects of maternal and fetal genotype in stress-induced PTB.

To investigate the effect of fetal genotype in addition to maternal genotype on stressed reduced gestation length, additional experiments were performed using FKBP51 knockout (KO) female mice mated with FKBP51 KO male mice, which resulted in complete (fetal and maternal) absence of FKBP51 expression during pregnancy. In these experiments, which are illustrated in FIG. 16, female mice were mated with male mice for only 4 hours. The presence of sperm in vaginal smear or vaginal plug was accepted as gestation day (GD) 0. Time-mated pregnant WT and KO mice were randomly assigned to either a stress or control group. Restrained stress was initiated on GD8 and continued until GD18. Time-mated WT and KO pregnant females were monitored between GD18-22, and delivery was checked at 4 hour intervals. The appearance of the first pup was considered the parturition time, and the number of born pups and their birth weights were recorded.

Figure 10:
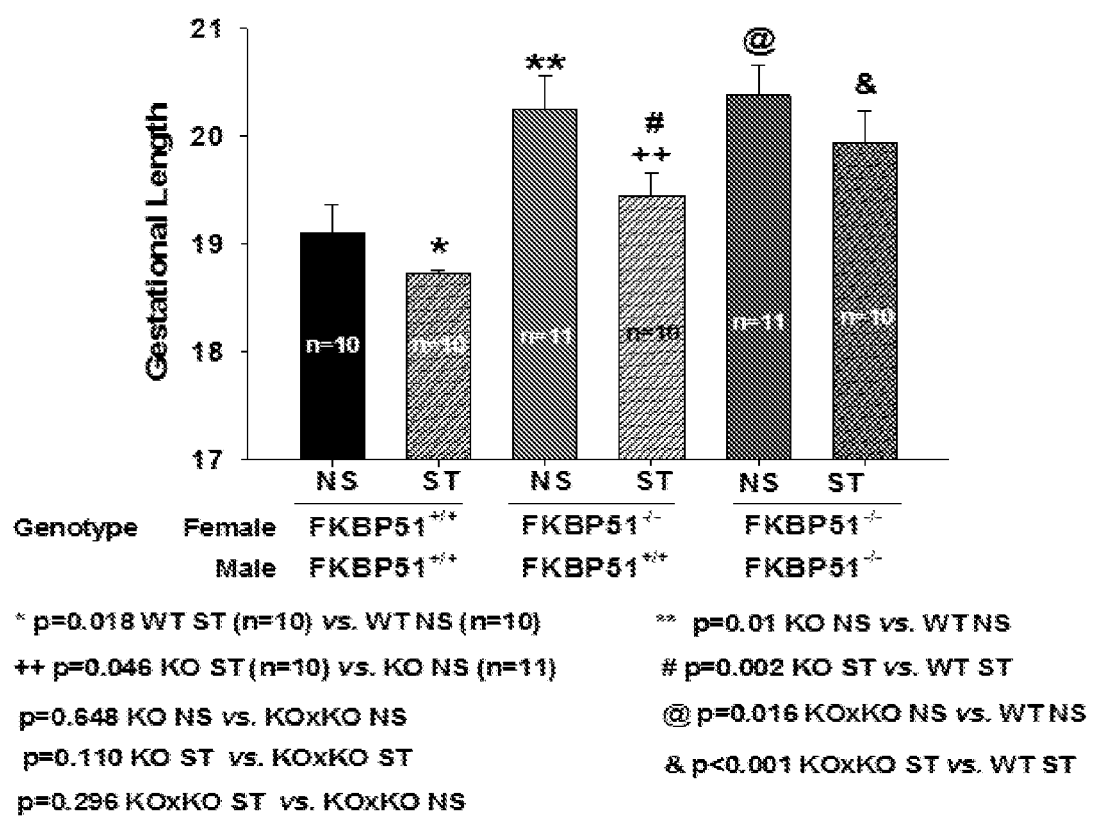
FIG. 10 is a graph showing the effects of maternal and fetal genotype on gestational length.

Mice with various maternal and fetal FKBP51 genotypes were compared to define the consequences of complete loss of FKBP51 on regulation of gestational length by restrained stress. These analyses revealed that restrained stress induced preterm birth (PTB) by significantly shortening gestational length in WT mice (p=0.018) as well as KO mice (p=0.046) mated with WT males. However, restrained stress did not induce PTB in FKBP51 KO mice (p=0.296) mated with KO males. These results indicated that pregnancies characterized by knockdown of maternal FKBP51 expression alone resulted in partial resistance to stress-induced PTB (see p values in FKBP51−/−vs. FKBP51+/+ mice; p=0.046 vs. p=0.018, respectively) and that stress-induced PTB was completely blocked in pregnancies characterized by knockdown of both maternal and fetal FKBP51 expression (p=0.296), as shown in FIG. 10.

Figure 11:
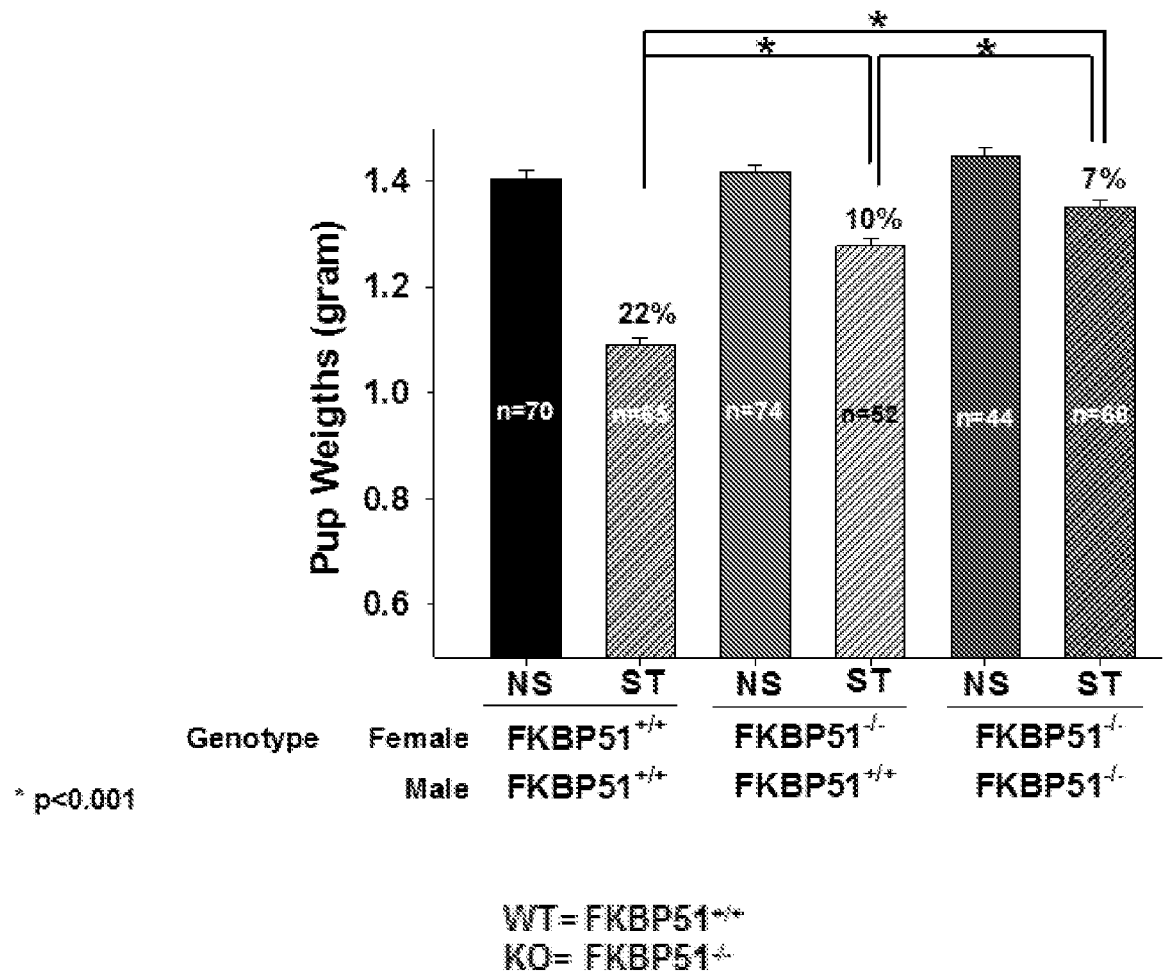
FIG. 11 is a graph showing the effects of maternal and fetal FKBP51 genotype on birth weight.

Pup weights in all non-stressed groups (WTxWT or KOxWT or KOxKO mated mice) were similar. However, restrained stress induced a significant reduction in pup weights in either WTxWT or KOxWT or KOxKO mice, as shown in FIG. 11. Specifically, pup weights were reduced by 22% in WT-stressed versus non-stressed WT mice, whereas this stressed-induced reduction in pup weight regressed to 10% in KO mice mated with WT males, with further significant regression to 7% in KO mice mated with KO males.

These results indicate that pregnancies characterized by knockdown of maternal FKBP51 expression alone significantly tolerated stress-induced FGR (FKBP51−/−vs. FKBP51+/+ mice 10% versus 22% stress-induced reduction in birth weights, respectively). Moreover, stress-induced fetal growth restriction (FGR) was further tolerated in pregnancies with complete (both maternal and fetal) knockdown of FKBP51 expressions (7% in KOxKO vs. 22% in WTxWT).

Example 4

This example demonstrates that stress induces rapid maternal serum progesterone (P4) withdrawal in WT mice, but not in FKBP51 KO mice.

In rodents, serum P4 withdrawal is associated with labor. To determine whether P4 withdrawal is impaired in pregnant FKBP51 KO mice, serum P4 levels were measured during the final 3 to 4 days of gestation prior to labor using a specific ELISA kit. Serum samples were collected from pregnant mice on gestation day (GD)16, GD17, GD18 and GD19 in WT non-stressed (WT-NST) mice, on GD16, GD17, GD18 and GD18.25 in WT-stressed (WT-ST) mice, and on GD17, GD18, GD19, GD19.75 in FKBP51 KO-NST or KO-ST mice.

Figure 12:
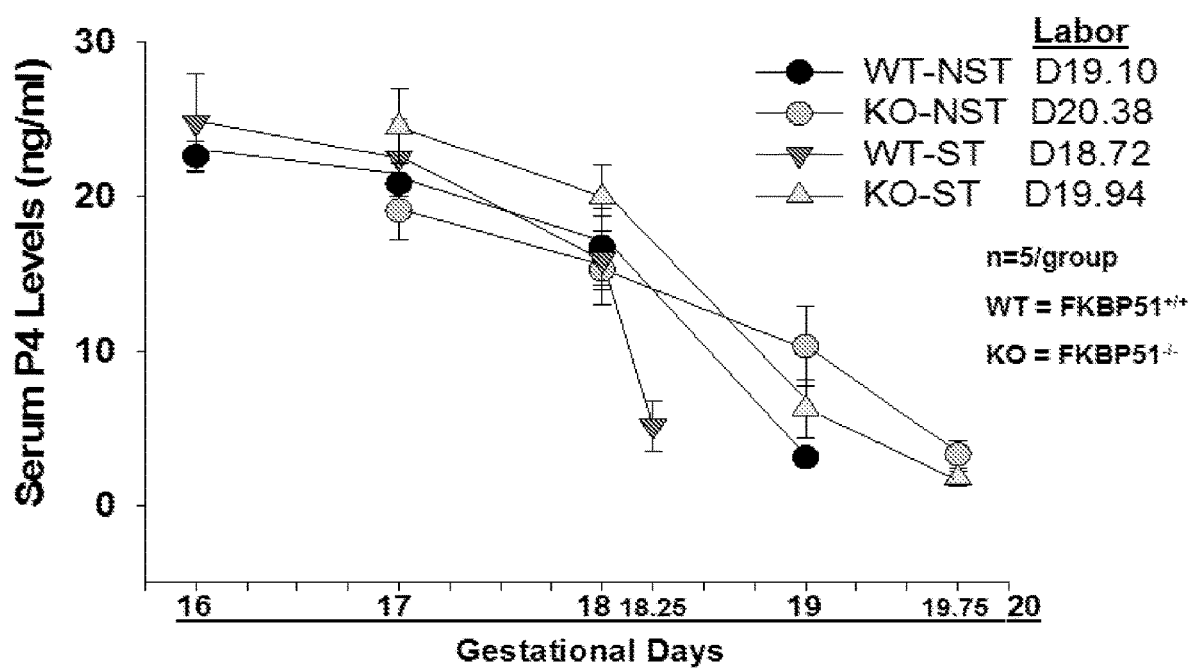
FIG. 12 is a graph showing P4 levels in WT and KO mice on gestation day (GD) 16 and GD20.
Figure 14A:
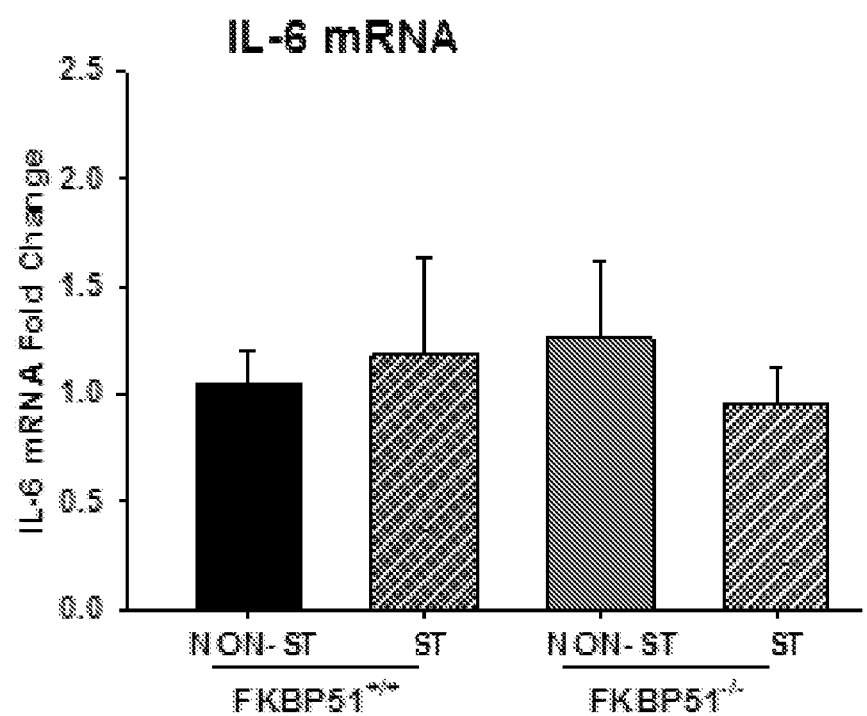
FIGS. 14A-14F are graphs showing placental expression of proinflammatory genes in WT and FKBP51 KO mice at day 18.25 (n=4/group). Genes analyzed included IL-6 (FIG. 14A), Cox-2 (FIG. 14B), IL-1β (FIG. 14C), IL-8 (FIG. 14D), MCP-1 (FIG. 14E), and TNF-α (FIG. 14F).
Figure 14B:
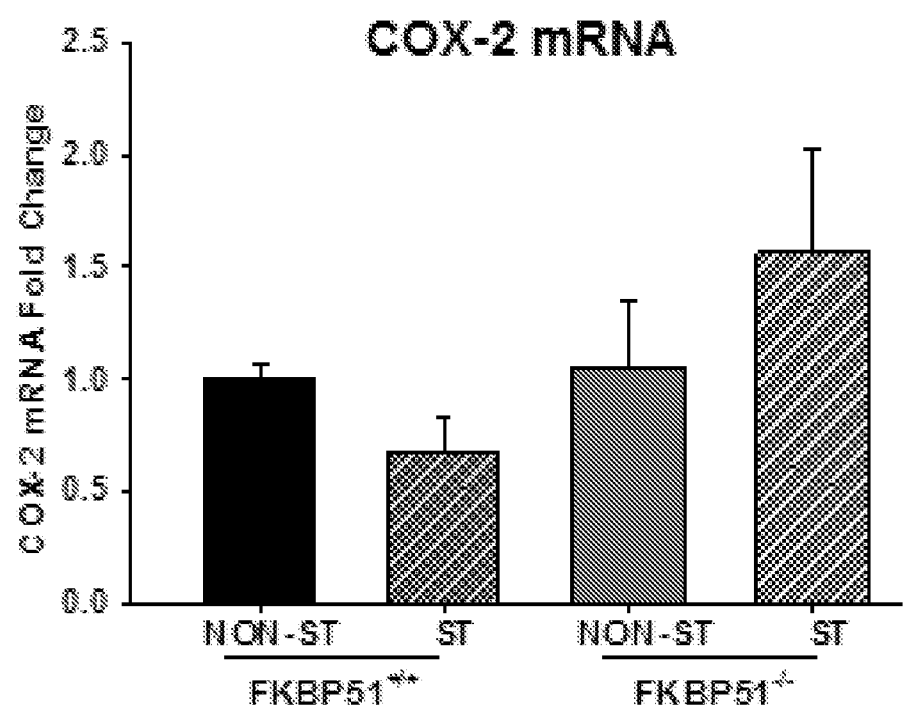
Figure 14C:
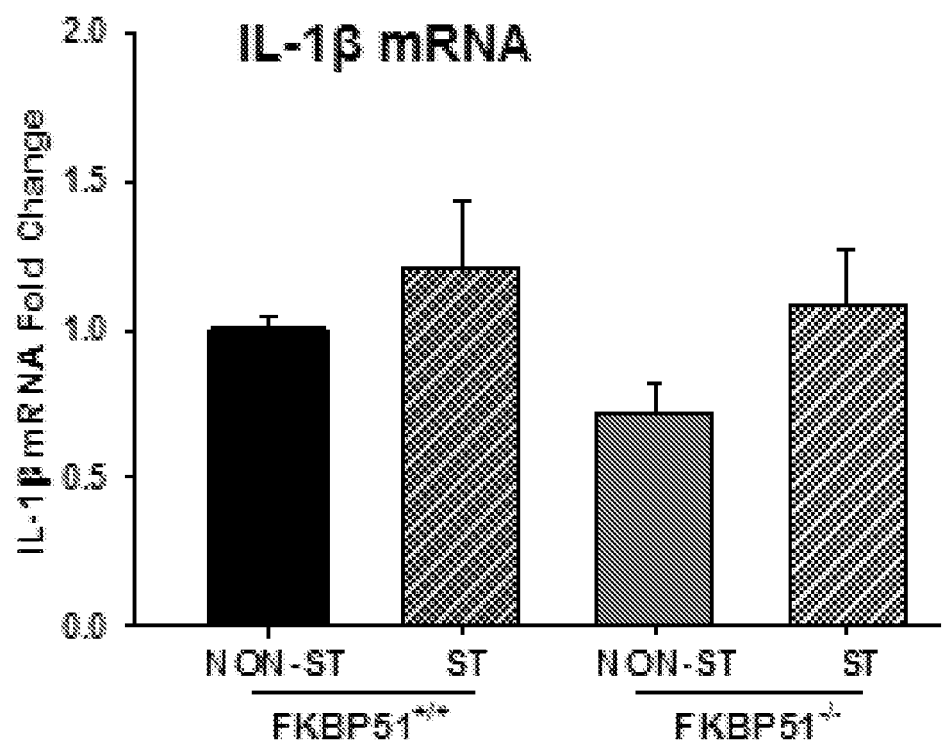
Figure 14D:
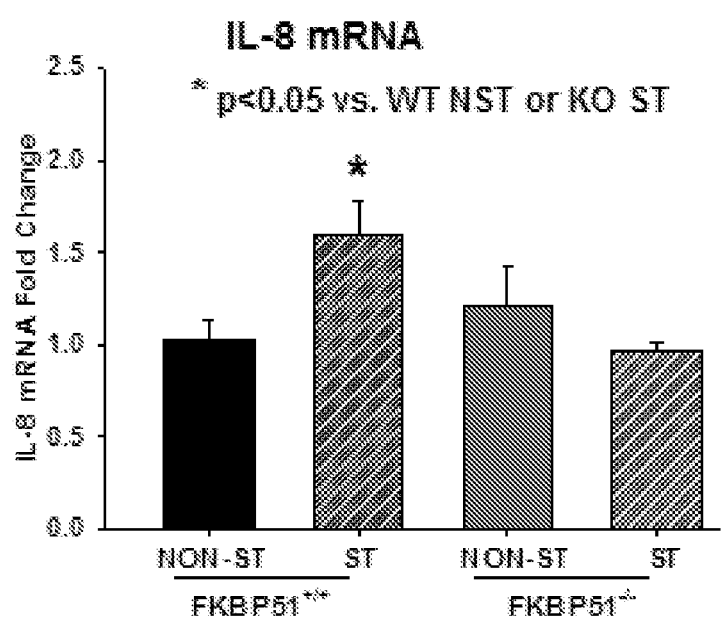
Figure 14E:
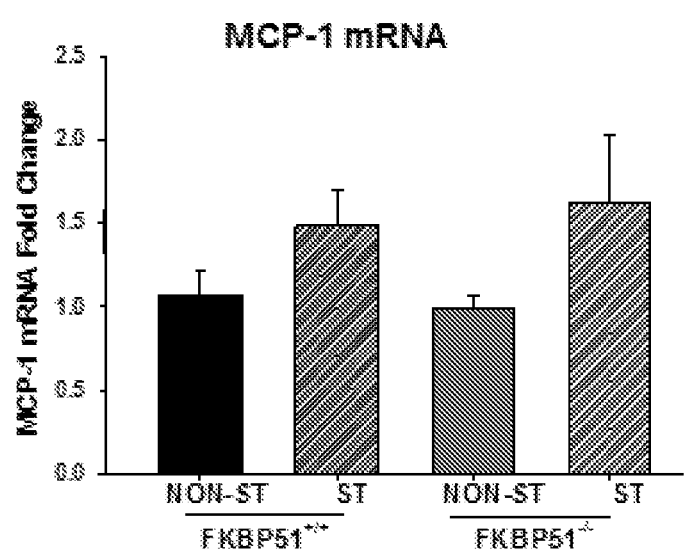
Figure 14F:
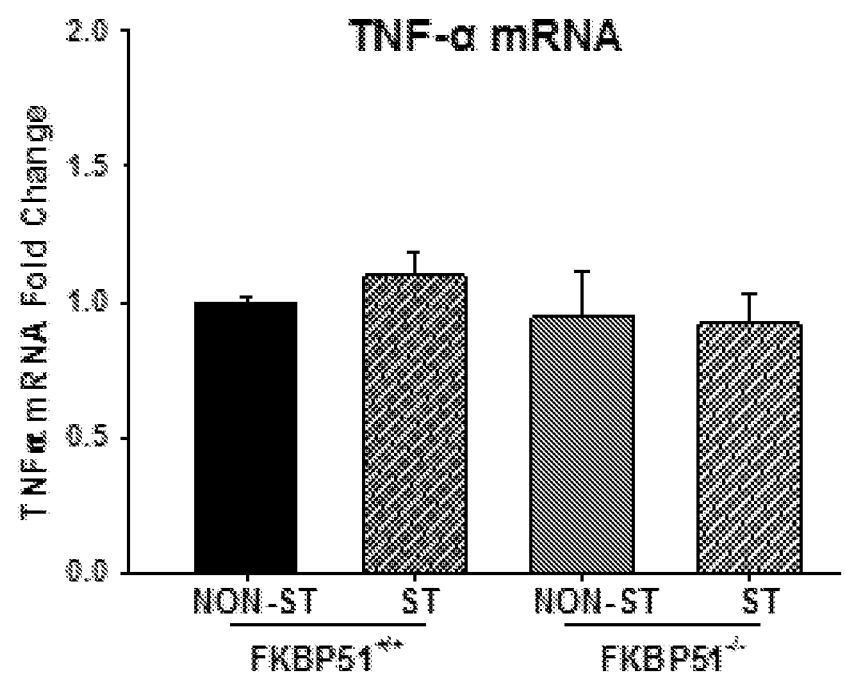

This analysis revealed that restrained stress induced a faster decline in maternal serum P4 levels in WT, but not in FKBP51 KO mice after GD18, as shown in FIG. 12. Moreover, serum P4 levels were significantly higher in KO-NST versus WT-NST on GD19, but not between KO-NST versus KO-ST mice on either GD19 or GD19.75. These results suggest that FKBP51 absence during pregnancy protects against stress-induced rapid P4 withdrawal, thereby maintaining pregnancy via sustained P4-PR signaling. This mechanism may be involved in preventing stress-induced PTB in FKBP51 KO mice.

Example 5

This example describes an analysis of placental progesterone receptor (PR) and glucocorticoid receptor (GR) gene expression in stressed and non-stressed mice.

RNA from mouse placentas (n=4) was extracted using an RNAEASY® Mini Kit (QIAGEN). One microgram of total RNA from each sample was reverse transcribed to complementary DNA (cDNA) using the Qmniscript Reverse Transcriptase Kit (Qiagen) and used for real time PCR to quantify the expression of several representative genes: PR, GR, IL-6, IL-8, MCP-1, IL-1β, and COX2, and β-actin as a reference gene. Quantitative RT-PCR analyses were performed using a TAQMAN® gene expression array using gene specific primer and probe (ABI 7500 thermocycler instrument). Experiments were performed in duplicate on 96-well PCR plates (ABI).

In order to determine the differences in target gene expression between WT and KO groups, a $2^{-\Delta\Delta CT}$ formula was used. The resulting normalized values were then used to estimate fold-changes between groups. These analyses showed that both PR and GR levels were significantly reduced in WT-ST mice compared to WT-NST, but not in KO-ST versus KO-NST (see FIGS. 13A and 13B). The qRT-PCR analyses also demonstrated significantly increased placental IL-8 mRNA levels in WT-ST mice versus WT-NST, but not in KO-ST versus KO-NST mice, as shown in FIGS. 14A-14F, suggesting that elevated IL-8 levels may increase neutrophil recruitment that likely contributes to stress induced-PTB.

These results suggest that the systemic rapid decline in P4 levels are accompanied by reduced placental PR and GR expression in WT-ST mice, resulting in amplified functional P4 withdrawal, thereby contributing to stress induced-PTB, which is prevented in both FKBP51 KO-NST or KO-ST by higher PR expression.

Example 6

This example describes an analysis of FKBP51 expression in primary term decidual cells (DCs) induced by dexamethasone (DEX) (0.1 µM) or 15dPGJ2 (5 or 20 µM) or DEX+15dPGJ2 (0.1 µM+5 or +20 µM).

Glucocorticoids (e.g. dexamethasone (DEX), medroxyprogesterone acetate) are primary inducers of FKBP51 mRNA and protein expression in decidual cells (DCs). It was determined that both restrained stress-induced preterm birth and fetal growth restriction are blocked in FKBP51 knockout mice compared to WT mice. To determine the potential therapeutic impact of 15-deoxy-Δ12,14-prostaglandin J2 (15dPGJ2) on regulation of dexamethasone-induced FKBP51, primary term DC cultures (n=1) were induced by DEX (0.1 μM), 15dPGJ2 (5 or 20 μM), or DEX+15dPGJ2 (0.1 μM+5 or +20 μM) for 24 hours, and FKBP51 protein levels were then analyzed by immunoblotting, as shown in FIG. 15A.

This analysis revealed that compared to control, DEX increased FKBP51 expression by 60%, whereas 5 μm and 20 μm 15dPGJ2 alone decreased FKBP51 expression by 10% and 18%, respectively, in term DC cultures. Furthermore, when combined with DEX treatment, 5 μm 15dPGJ2 reduced DEX-induced FKBP51 expression by 12%, with 20 μm 15dPGJ2 completely blocking DEX-induced FKBP51 expression, as shown in FIG. 15B.

Taken together, these results suggest the therapeutic utility of 15dPGJ2 and its derivatives in preventing preterm birth and FGR.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of extending the gestation period of a mammal comprising administering a composition comprising an inhibitor of FK506 binding protein 51 (FKBP51) to a pregnant mammal, whereby the gestation period of the pregnant mammal is extended as compared to a mammal that is not administered the composition, wherein the inhibitor of FKBP51 is 15-deoxy-Δ12,14-prostaglandin J2 or a small interfering RNA (siRNA), wherein the pregnant mammal is under stress, wherein the pregnant mammal has an increased level of IL-8 as compared to a reference control, and wherein the pregnant mammal does not have an increased level of IL-6 as compared to a reference control.

2. The method of claim 1, wherein the inhibitor of FKBP51 enhances progesterone receptor (PR) activity in the mammal as compared to a mammal not administered the composition.

3. The method of claim 2, wherein the PR activity is PR-mediated gene transcription.

4. The method of claim 1, wherein the mammal is a human female.

5. The method of claim 1, wherein the likelihood of preterm birth (PTB) is reduced as compared to a mammal that is not administered the composition.

6. The method of claim 1, wherein the pregnant mammal does not have an increased level of TNF-α as compared to a reference control.

* * * * *